United States Patent [19]

Bennett

[11] Patent Number: 5,156,160
[45] Date of Patent: Oct. 20, 1992

[54] ADJUSTABLE BIOPSY DEVICE CAPABLE OF CONTROLLING TISSUE SAMPLE SIZE COLLECTED THEREBY

[76] Inventor: LaVon L. Bennett, 130 W. Center, Alpine, Utah 84004

[21] Appl. No.: 542,324

[22] Filed: Jun. 22, 1990

[51] Int. Cl.$^5$ ............................................. A61B 10/00
[52] U.S. Cl. .................................................... 128/754
[58] Field of Search ............... 128/749, 751, 753, 754, 128/757; 604/21

[56] References Cited

U.S. PATENT DOCUMENTS

| | | | |
|---|---|---|---|
| 2,516,492 | 7/1950 | Turkel | 128/751 |
| 2,818,852 | 1/1958 | Kugler | 128/755 |
| 3,989,033 | 11/1976 | Halpern et al. | 128/754 |
| 4,243,048 | 1/1981 | Griffin | 128/751 |
| 4,461,305 | 7/1984 | Cibley | 128/754 |
| 4,699,154 | 10/1987 | Lindgren | 128/754 |
| 4,763,667 | 8/1988 | Manzo | 128/754 |
| 4,776,346 | 10/1988 | Beraha et al. | 128/754 |
| 4,881,551 | 11/1989 | Taylor | 128/754 |
| 4,893,635 | 1/1990 | de Groot et al. | 128/754 |
| 4,944,308 | 7/1990 | Akerfeldt | 128/751 |
| 5,014,717 | 5/1991 | Lohrmann | 128/754 |

FOREIGN PATENT DOCUMENTS 459635 7/1989 Sweden ............... 128/751

OTHER PUBLICATIONS

The Bard Monopty ™ Biopsy System (no date).

*Primary Examiner*—Max Hindenburg
*Attorney, Agent, or Firm*—Terry M. Crellin

[57] ABSTRACT

A tissue sampling device comprises an inner rod and an outer cannula. A primary piston is attached to a hub on the proximal end of the rod, and a secondary piston is attached to a hub on the proximal end of the cannula. The primary and secondary pistons are coupled to an actuator including a double locking mechanism and a pair of springs. The springs engage the primary and secondary pistons, and the locking mechanism holds the pistons in a cocked position. Upon triggering, the primary piston moves in response to the spring associated therewith. This moves the rod a corresponding distance causing a predetermined length of a sampling notch at the distal end of the rod to extend from the distal end of the cannula and penetrate tissue in the sample target area. Following the movement of the primary piston, the secondary piston is released from the locking mechanism, and the secondary piston moves in response to the spring acting thereon. This moves the cannula along the inner rod, and the sharpened end of the cannula severs tissue in the exposed portion of the notch of the rod and captures the severed tissue as the cannula moves over the exposed portion of the notch. The movement of the primary piston is adjustable, so that the length of the notch exposed to tissue can be controlled thereby allowing adjustable control of the amount of tissue sample that is severed and removed from the target area.

11 Claims, 5 Drawing Sheets

ADJUSTABLE BIOPSY DEVICE CAPABLE OF CONTROLLING TISSUE SAMPLE SIZE COLLECTED THEREBY

BACKGROUND OF THE INVENTION

1. Field of the Invention

This invention relates generally to an apparatus and method for sampling tissue. More specifically, the present invention relates to a biopsy device which can be adjusted to allow precise amounts of sample tissue to be collected thereby.

2. Prior Art

The removal of minute tissue samples from humans and animals by introducing a needle into the body and catching the sample within the needle, is a frequently used medical practice today. Such samples are necessary for microscopic examination, organ cultures, etc.

The method most commonly followed for obtaining tissue samples has been to use a needle which is formed of an inner solid rod which has a sampling notch in the distal end thereof, in conjunction with a hollow outer cannula which slides thereover and cuts tissue which has been located in the sampling notch of the inner rod. The inner rod, except for its pointed distal end, is located within the cannula when the device is inserted into the tissue to be sampled. The outer cannula is then held stationary while the inner rod is inserted deeper into the tissue. While in this position, tissue moves into the sampling notch of the inner rod just adjacent the pointed distal tip thereof. The inner rod is then held stationary while the outer cannula is slid thereover. Motion of the outer cannula passing over the sampling notch causes the tissue located therein to be severed from surrounding tissue and thereafter to be trapped in the sampling notch as the cannula completely covers the inner needle distal end. Both the outer cannula and the inner rod with the tissue sample secured therein are then simultaneously removed from the patent. The outer cannula is then slid back away from the distal end of the inner rod to allow removal of the tissue sample from the sampling notch thereof. The tissue sample is then examined.

This general method of tissue sampling has been used for several decades and is exemplified in U.S. Pat. No. 3,477,423. As disclosed therein, the needle movements are made manually. This has certain disadvantages, in that movements may not be made fast enough to insure clean and complete severance of a tissue sample. Further, manual operation of the needle generally involves inaccurate movements, and slight lack of coordination between the needle and the cannula. This often causes unnecessary tissue damage and, in the case of infectious or tumorous tissue, can cause spreading of the diseased tissue throughout a larger tissue area. Also, during manual operation of a needle, the patient may move slightly during the introduction thereof into the tissue and cause the needle to its target area. Also, respiratory movements are common for some organs, for example the liver and the kidney, which further may reduce the accuracy of the sampling technique.

An improvement in the above mentioned method of biopsy sampling has been to restrict needle movements by containing the inner rod and outer cannula inside a holder. The holder restricts needle movement to specific directions and also may carry springs therein which drive the rod and cannula through their sampling motions in a rapid and predictable manner. This technique is exemplified in U.S. Pat. No. 4,699,154. Even though this is an improvement over manually actuated needles, it nevertheless carries several disadvantages. For example, the length of the needle movement cannot be adjusted according to the size of the sample desired to be taken. Therefore, unnecessary quantities of tissue may be removed from the tissue sample area causing unnecessary tissue damage and possibly unnecessary spreading of diseased tissue. Further, the forceful introduction of a needle into the tissue area generally causes a certain amount of damage to the tissue in the immediate surroundings of the target area. This is due to the high pressure released from the needle in the injection process.

Therefore, there has long existed a problem in the prior art of controlling the size of a tissue sample taken by the biopsy needle. The size of the sample should not exceed the necessary amount of tissue needed for diagnostic purposes. Since prior art devices have included no ability to adjust the size of sample taken in an accurate manner, they have failed to resolve this problem. Also, a smaller tissue target area, such as a lesion or tumor or the like should be sampled with a shorter movement of the needle and a smaller and more controlled sample size taken thereby. This is because the needle should not pass outside the target area into unaffected area of the tissue, nor should it reach outside of the organ, tumor, lesion, etc. which is being sampled to thereby cause risk of damage to other structures such as adjacent large blood vessels or the like. It is therefore needful to develop an apparatus where the needle movements can be precisely made to allow the physician to collect precisely the desired tissue sample volume predetermined with various imaging methods (e.g. radiological, ultrasound or computer tomography examination) without unnecessary damage to the tissue or surrounding structures.

OBJECTS AND SUMMARY OF THE INVENTION

It is an object of the present invention to provide a tissue sampling apparatus which allows for precise control of the tissue sample volume collected thereby.

It is another object of the present invention to provide a tissue sampling device which is adjustable so that various tissue sample sizes may be collected by the same apparatus depending on the pre-set adjustment thereto.

It is another object of the present invention to provide a tissue sampling device which significantly limits the damage to tissue and surrounding structure during sample collection.

It is further an object of the present invention to provide a tissue sampling device which is easily handable by one hand of the user, and is automatically actuatable for increased control and accuracy of sample taking.

It is also an object of the present invention to provide a tissue sampling device which employs a sampling needle having an inner rod and outer cannula wherein the inner rod contains a sampling notch and in which the apparatus can control the depth of penetration of the inner rod into the sampling target area in order to control the volume of tissue sample collected.

These and other objects of the present invention are embodied in a method and apparatus for tissue sampling which allows for precision control of tissue sample size in accordance with the requirements of the diagnostic procedure to which the tissue sample is to be submitted. Precise control of tissue sample size allowing for minimization of the damage caused by the sampling needle, and for simplicity in operation.

The invention as shown in one preferred embodiment thereof includes an elongated generally cylindrical biopsy device having a pair of piston like moveable elements. The primary piston includes an attachment chamber thereon for holding the hub portion of an inner rod of a biopsy needle, the secondary piston including a similar chamber for attachment to the hub portion of the outer cannula portion of a biopsy needle. The pistons extend from the biopsy device in a manner which allows for the attachment of the biopsy needle into the chambers, with the inner rod thereof slidably located within the outer cannula. The opposite ends of the pistons are located within the biopsy device and are spring loaded to a uniquely designed releasing mechanism which, when triggered a first stage of actuation extends the first piston (and thereby the inner rod of the biopsy needle) a predetermined distance into a tissue sample target area. The completion of motion of the primary piston completes the first stage of actuation and also causes a secondary triggering, which then moves the secondary piston in the same direction of motion as the primary piston previously moved, thus moving the outer cannula to sever tissue in the sample notch of the inner rod as it re-extends thereover.

The primary piston is adjustable in its distance of travel by a threaded washer which can be adjustably positioned on the proximal end thereof. Motion of the primary piston due to triggering of the first stage of actuation causes the threaded washer to move into abutment against a the triggering mechanism, for the second stage of actuation just prior to the completion of the travel distance pre-set for the primary piston. The adjustment setting of the washer is easily determined by markings on the exterior portion of the secondary piston, much in the manner common to well known micrometer designs.

The triggering mechanism includes a triggering knob which is located externally of the biopsy device and which, when depressed actuates the first stage of the actuation process which moves the primary piston its predetermined distance. Motion of the primary piston is arrested by the adjusted washer as previously described. The second phase of the actuation mechanism is initiated by the washer at the completion of its travel. The second stage is therefore prevented from proceeding until the first stage has completed its motion. The second phase of the actuation mechanism releases the secondary piston to allow the spring associated therewith to move the secondary piston to the position relative to the primary piston which it had before initialization of actuation.

DETAILED DESCRIPTION OF THE PREFERRED EMBODIMENT

Figure 1:
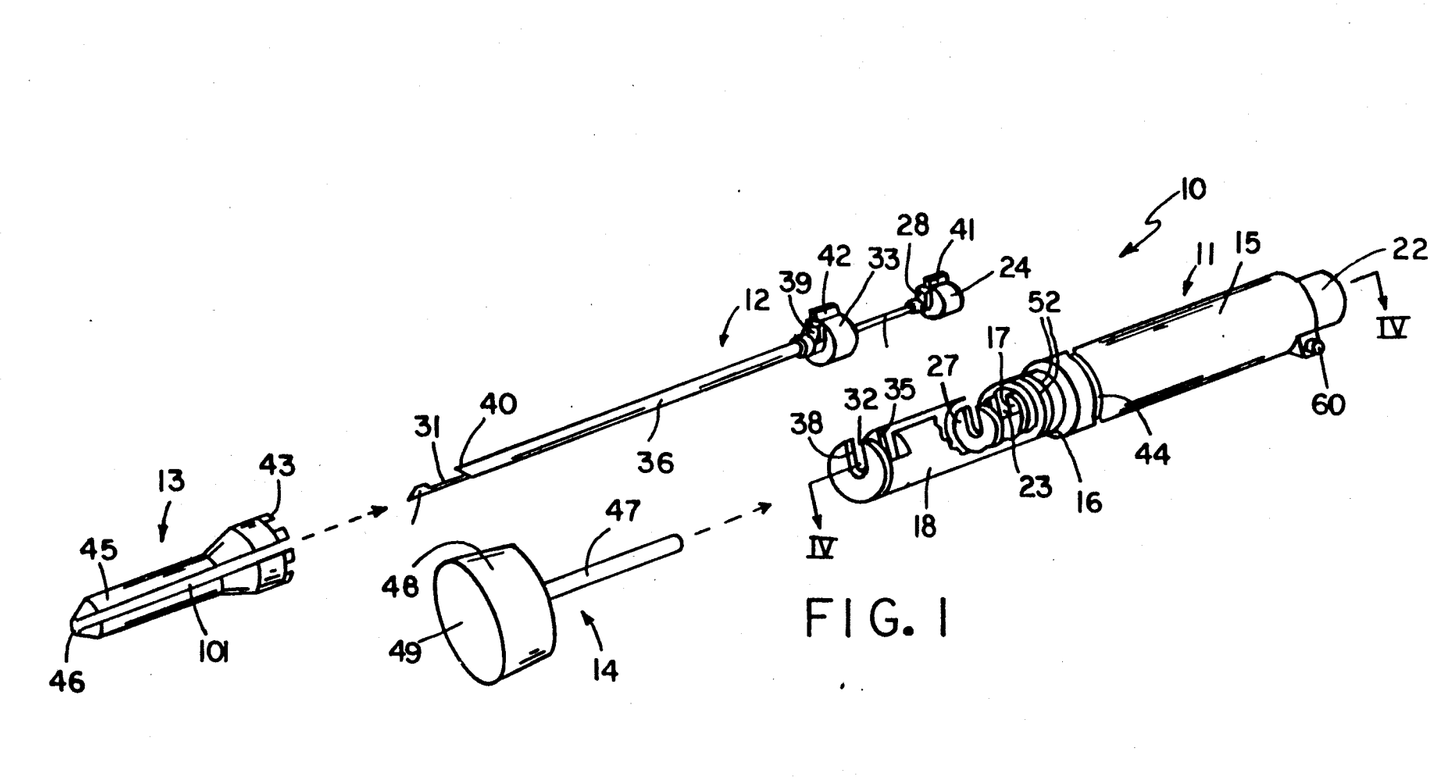
FIG. 1 is an expanded prospective view of a biopsy device made in accordance with the principles of the present invention.
Figure 2:
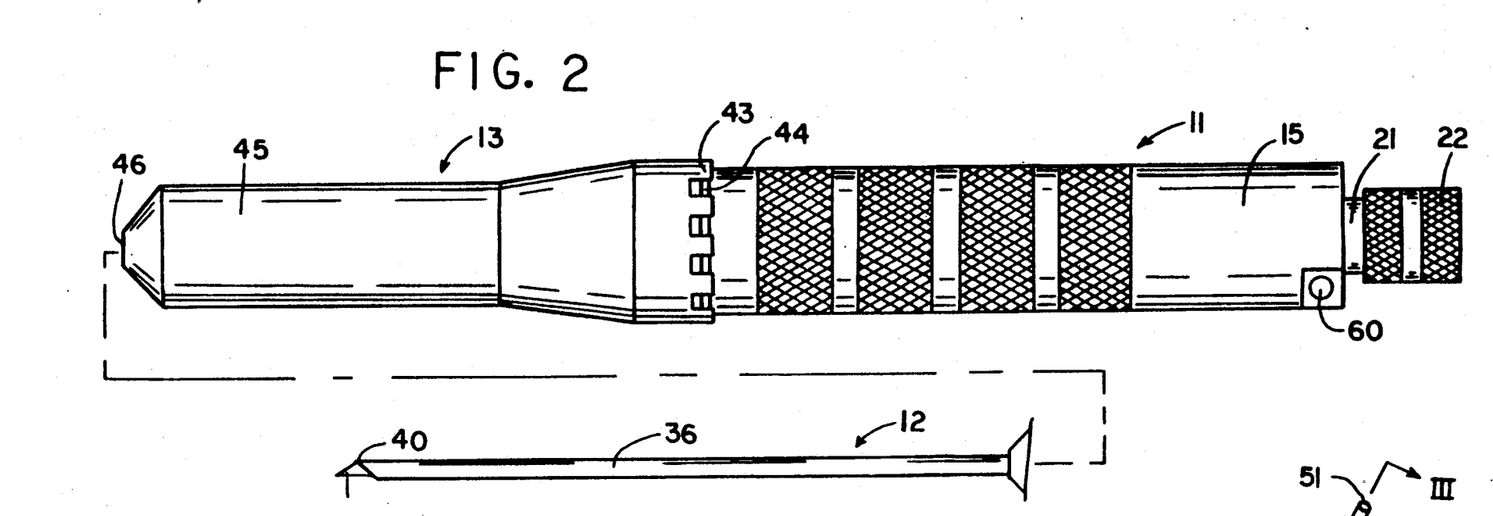
FIG. 2 is a side view of the biopsy device of the present invention.

As shown in FIG. 1, the biopsy device 10 of the present invention is composed generally of an actuator mechanism 11, a needle 12, and a cover 13. The needle 12 is adapted to be inserted into the actuator mechanism 11, with the cover 13 being formed to pass over the needle and attached to the actuator as shown in FIG. 2.

The cocking mechanism 14 (as shown in FIG. 1) is a necessary accessory to the biopsy device 10, although it is never physically attached to the biopsy device 10 during its operation. The cocking mechanism 14 is used only for resetting the actuator mechanism 11 to its "cocked" position after each actuation thereof. The manner in which this is to be done will be explained momentarily.

Actuator mechanism 11 is formed of a generally cylindrical housing 15 which has a distal opening 16 therein through which protrudes the distal ends of a primary piston 17 and a secondary piston 18. The housing 15 also has an opening 20 in its proximal end through which a triggering and adjustment shaft 21 extends, the triggering and adjustment shaft 21 having triggering and adjustment knob 22 affixed thereto. The housing 15 and the triggering and adjustment knob 22 may be knurled on their outer cylindrical surface so as to improve their appearance and gripability during use.

Figure 4A:
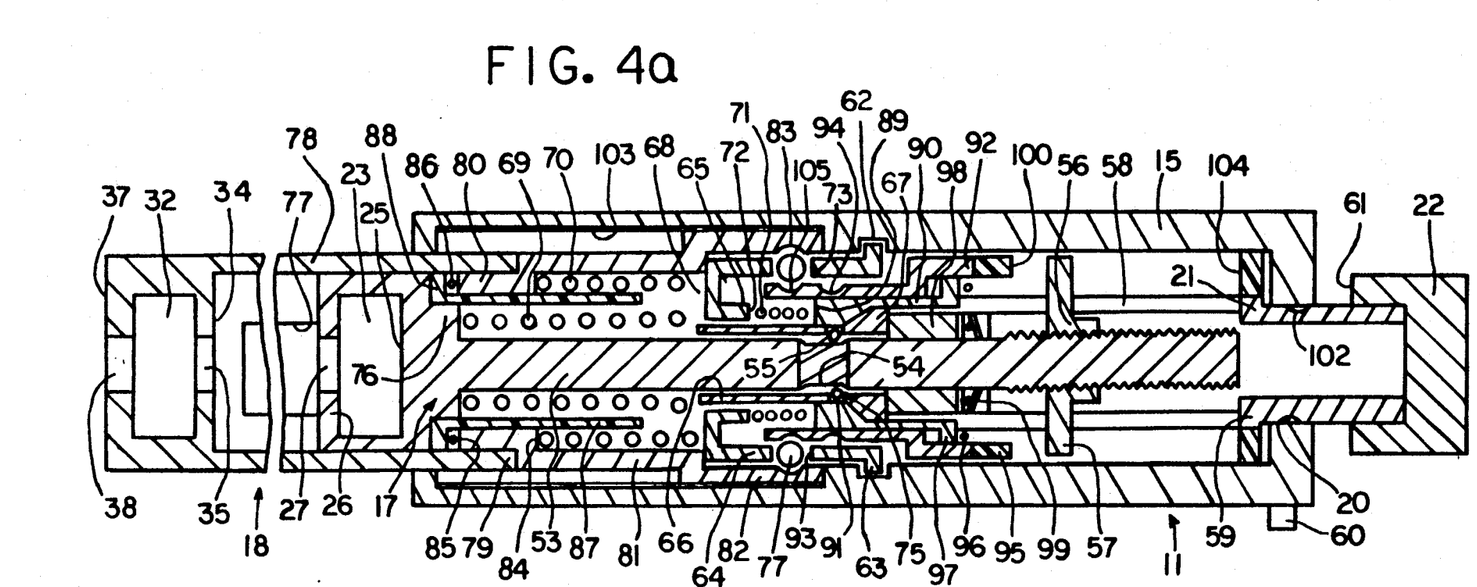
FIG. 4(a) is a cross sectional view of the biopsy device of the present invention taken along line IV—IV of FIG. 1.

As best shown by FIGS. 1 and 4(a), the distal end of primary piston 17 forms a generally cylindrical hub channel 23 which is sized to allow hub 24 of the needle 12 to be laterally inserted therein. The hub channel 23 includes a bottom plate 25 against which the proximal end of hub 24 rests when located in hub channel 23. Top plate 26 of hub channel 23 has included therein an orientation grove 27 which is of a generally U-shaped configuration and which is sized to accept the generally U-shaped surface of orientation shoulder 28 of hub 24. The orientation groove shoulder 28, when forced into conjunction with orientation groove 27, forces the hub 24 to be located in hub channel 23 in a single specific orientation. As best seen in FIG. 1, this orientation causes the pointed distal tip 29 of the inner rod 30 of the needle 12 to be fixed in its shown orientation relative to the actuator mechanism 11.

Similarly, secondary piston 18 includes a hub channel 32 at its distal end which can accept hub 33 of the needle 12. Bottom plate 34 of channel 32 includes a generally U-shaped needle groove 35 therein which allows passage of the inner rod 30 into hub channel 32 and through the hollow cannula 36 of the needle 12. The top plate 37 of hub channel 32 includes a generally U-shaped orientation groove 38 which cooperates with orientation shoulder 39 of hub 33 to force hub 33 into only one possible orientation relative to actuator mechanism 11, and therefore, into a single fixed orientation relative to inner rod 30.

The sharp distal end 40 of cannula 36 is formed at an angle relative to the longitudinal axis of cannula 36, with the most distal tip thereof being forced into orientation such that it is located directly over the sampling notch 31 of the inner rod 30. With the relative orientations of inner rod 30 and cannula 36 forced thereon due to the insertion of needle 12 into actuator mechanism 11, the distal ends of inner rod 30 and cannula 36 are oriented such that a tissue sample collected in sample notch 31 will be cleanly and effectively cut from its surrounding tissue as the distal end 40 of cannula 36 slides over the inner rod 30 in the direction of the pointed distal tip 29 thereof.

Each of hubs 24 and 33 of the needle 12 include an elongated brace member 41 and 42 respectively located thereon, which extend radially from the cylindrical surface of each hub. When the needle 12 is correctly located in the actuator mechanism 11, the braces 41 and 42 extend directly above the hub channels 23 and 32. The braces 41 and 42 are sized so as to have their top surface in contact with an imaginary surface defined by a cylinder corresponding to the diameter of secondary piston 18. When cover 13 is inserted over needle 12, the cannula 36 and inner rod 30 of the needle 12 pass through the slot 101 and extend through the distal opening 46 thereof. The cover locking members 43 are then attached in housing locking groove 44 in the manner as shown in FIG. 2. In this position the cylindrical body portion 45 thereof contacts the outer surface of the secondary piston 18 and also the top surfaces of braces 41 and 42. Although cover 13 is shown as connecting to the housing 15 by means of locking members 43, it is well within the scope of the invention to attach the cover 13 in any well known manner.

The cover 13 has several functions. First, it is sized so as to contact the cylindrical surface of secondary piston 18 and the top surfaces of braces 41 and 42 in order to securely hold the hubs 24 and 33 in their proper position in their respective hub channels 23 and 32. Secondly, the cover 13 functions to completely cover the extending portions of the primary and secondary pistons 17, and 18, and the hubs 24 and 33, so that a user may grip the biopsy device 10 in any comfortable and convenient manner during operation without concern for interfering with any moveable parts, or any internal workings thereof. Finally, the cover 13 aids in keeping the needle 12 sterile during use.

Figure 3A:
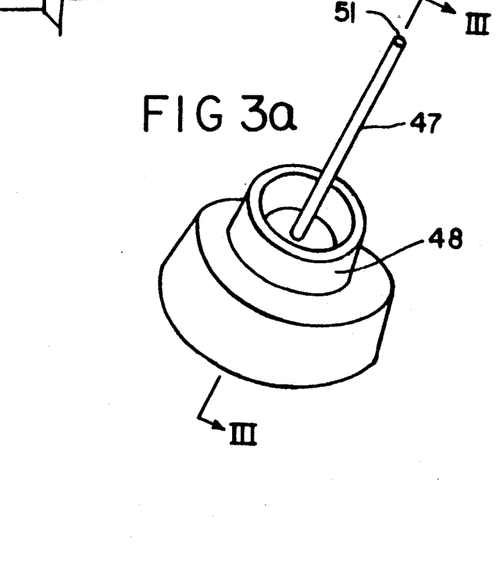
FIG. 3(a) shows the cocking mechanism used in conjunction with the biopsy device of the present invention.
Figure 3B:
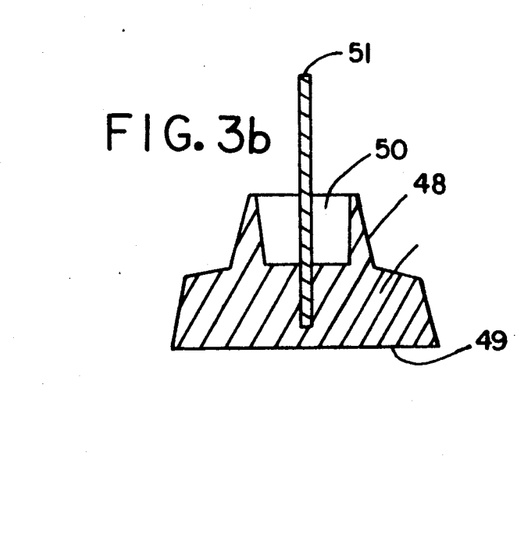
FIG. 3(b) is a cross-sectional view of the cocking mechanism taken along line III—III of FIG. 3(a)

The cocking mechanism 14 of the invention is most clearly shown in FIGS. 3(a) and 3(b). The mechanism 14 includes a cocking peg 47 which is secured in a generally cylindrical base 48. The base 48 may be flat on its bottom surface 49 so that it can be placed on any flat surface when in use. The bottom surface 49 is generally perpendicular to the longitudinal axis of the cocking peg 47 so that forces along the axis of peg 47 do not cause the cocking mechanism 14 to be displaced during the cocking procedure. Base 48 may also include a cavity 50 therein which allows the distal portion of the secondary piston 18 to be inserted therein for additional stability in the cocking process.

Operation of the biopsy device 10 of the present invention is as follows. First, the trigger and adjustment knob 22 of the actuator mechanism 11 is rotated until the desired travel distance of the primary piston 17 is set. This is easily verified by turning the travel adjustment knob 22 until the desired number of adjustment calibration lines 52 are visible and are directly adjacent to the distal housing opening 16. It is contemplated that the adjustment calibration rings be circumferentially located around the cylindrical surface of the secondary piston 18, and spaced such that the first ring 52 corresponds to approximately 6 mm of travel of the primary piston 17 during actuation of the device 10, and each incremental calibration ring 52 thereafter corresponding to an additional 2 mm increments of travel distance. These distances are not critical however, any desired incremental distances may be employed.

The cocking mechanism 14 is placed such that its bottom surface 49 is located on a flat horizontal surface as a table or the like. The actuator mechanism 11 is then oriented such that its longitudinal axis is aligned with the longitudinal axis of cocking peg 47. The cocking peg 47 is then inserted through the orientation groove 38 and needle groove 35 of the secondary piston 18 and through the orientation groove 27 of primary piston 17 until the end 51 of the cocking peg 47 contacts bottom plate 25 of hub channel 23 in primary piston 17.

A downward force is then applied to the actuator mechanism 11 along the longitudinal axis of peg 47 causing primary piston 17 to be forced into housing 15 until the internal elements of actuator mechanism 11 lock the primary piston 17 in its "cocked" position. As will be later explained, the motion of the primary piston into the housing 15 also causes the secondary piston 18 to be drawn into the housing 15 and locked in its "cocked" position.

Once the actuator mechanism 11 is cocked, the cocking mechanism 14 is removed therefrom and safety mechanism 60 is set. Needle 12 is then inserted into the actuator mechanism 11 by inserting rod hub 24 and cannula hub 33 into primary piston hub 23 and secondary piston hub 32 respectively. The hubs 24 and 33 being oriented such that orientation shoulders 28 and 39 thereof will correctly pass into orientation grooves 27 and 38 respectively, with inner rod 30 passing through needle groove 35 of hub channel 32 and through cannula 36. With the actuator mechanism 11 in its cocked position, the pointed distal tip 29 of inner rod 30 will extend just slightly beyond the distal end 40 of cannula 36 and the sample notch 31 will be completely covered by the cannula 36 (see FIG. 2 and FIG. 4(b)).

Cover 13 is then inserted over needle 12 such that cannula 36 and inner rod 30 pass through distal opening 46 thereof. The cover 13 is passed along the needle 12 until cover locking members 43 lock in position in housing locking groove 44. The biopsy device 10 of the present invention is then configured in the manner as shown in FIG. 2 and is ready to be used to collect a tissue sample.

The user then inserts the needle 12 into the tissue to be sampled until the pointed distal tip 29 thereof rests directly adjacent the sample target area. This may be done in any conventional manner and in conjunction with any well known equipment used for aiding the user in correctly locating the needle in the tissue. For example, a guide lumen may be used to aid in insertion of the needle 12 into the tissue, and/or, ultrasound equipment generating an internal image of the tissue may be used to assist the user in correctly locating the needle 12 at the target area.

When the user is ready to obtain a tissue sample, the trigger and travel adjustment knob 22 is pushed towards the housing 15. The trigger initiates an automatic, two-stage actuation process of the needle 12. The internal elements of actuator mechanism 11 which carry out the two-stage actuation will be explained later. The first stage of actuation causes inner rod 30 to travel in a distal direction through cannula 36 such that the pointed distal tip 29 thereof penetrates the tissue target area tissue to be sampled, and the sample notch 31 extends beyond the distal end 40 of cannula 36 and becomes exposed to tissue in the target area. The inner rod 30 travels the fixed travel distance which was preset by the actuator mechanism 11 before it was cocked. Since the inner rod 30 can travel only the predetermined travel distance, only a predetermined length of the distal end of the inner rod 30 will extend beyond the distal end 40 of cannula 36. Subsequently, only a predetermined length of the sample notch 31 will be exposed to tissue in the target area.

Tissue immediately fills sample notch 31 as it becomes exposed thereto, which completes the first stage of actuation. The second actuation stage causes cannula 36 to move in a distal direction along now stationary rod 30. The distal motion of cannula 36 causes the sharpened distal end 40 thereof to sever tissue located in sample notch 31 away from the surrounding tissue in the target area. Cannula 36 continues its motion in the distal direction until it returns to its previous position directly adjacent the distal tip 29 of the inner rod 30. When in this position, the second and final stage of the actuation is complete.

The user then removes the needle 12 from the tissue. The cover 13 is removed from the housing 15 and slid completely off the needle 12. The needle 12 is then removed from the actuator mechanism 11. The entire needle 12 can then be placed in a receptical which can then be sent to a laboratory or other location for evaluation of the collected tissue sample. The tissue sample itself remains in the sample notch 31 and remains covered by cannula 36. The tissue sample is therefore stored exactly as it was collected until actual evaluation of the tissue sample is ready to take place.

If desired, a safety mechanism 60 may be included in the housing 15 of the actuator mechanism 11. The safety mechanism 60 functions in a well-known manner to prevent any relative motion between housing 15 and trigger and travel adjustment knob 22 until it is specifically desired to trigger the actuator mechanism 11. The safety mechanism 60 may include an elongated cylinder which has a first and second position. The first position directly interfering with a channel 102 and thus preventing motion of the trigger and adjustment shaft 21 relative to housing 15; and the second position of the safety mechanism 60 offering no interference with the motion of shaft 21 with respect to housing 15. It is contemplated that any well-know safety mechanism be used in conjunction with the present invention if desired, although it should be noted that a safety mechanism is not required for proper operation thereof.

The internal workings of the actuator mechanism 11 will now be explained. FIG. 4(a) is a cross-sectional view of the actuator mechanism 11 showing the integral workings thereof in their "cocked" position. The primary piston 17 includes a piston shaft 53 which extends substantially the entire length of the housing 15 of the actuator mechanism 11. The distal end of the primary piston shaft 53 which extends substantially the entire length of the housing 15 of the actuator mechanism 11. The distal end of the primary piston shaft 53 is formed into the hub channel 23 as has been previously explained. The central portion of the primary piston shaft 53 has a reduced diameter portion 54 into which a plurality of primary catch balls 55 are located. A proximal end of the primary piston shaft 53 is threaded and includes thereon a primary stroke adjustment washer 56 which is also threaded. The stroke adjustment washer 56 includes a plurality of wing members 57 which are located in slots 58 of the generally cylindrical trigger and adjustment shaft 21. Opening 20 of housing 15 allows the proximal end of the trigger and adjustment shaft 21 to pass out thereof and be rigidly attached to trigger and travel adjustment knob 22.

Shoulder 59 of shaft 20 is located just inside the housing 15 and is of a diameter slightly greater than opening 20. A plastic bushing 104 is located between shoulder 59 and the interior of housing 15 in order to improve the friction resistance therebetween so that the shaft 21 remains in the position it is set to. Shaft 21 thus is allowed to slide through opening 20 in the proximal direction until shoulders 59 contact the inner surface of housing 15 and in the distal direction until the bottom surface 61 of trigger 22 contacts the outer surface of housing 15. The total distance which shaft 21 is allowed to slide through opening 20 corresponds to the distance necessary for the shaft 21 to properly trigger the internal workings of the actuator mechanism 11 as will be explained below.

Triggering an adjustment shaft 21 is also allowed to freely locate in opening 20. Wings 57 of the primary travel adjustment washer 56 are confined in slots 58 of the shaft 21 and thus cause the washer 56 to rotate relative to primary piston shaft 53 when trigger and adjustment shaft 21 is rotated by the rotation of knob 22. Since washer 56 is threadedly attached to primary piston shaft 53, relative rotation thereof causes washer 56 to move distally or proximally along the longitudinally axis of the actuator mechanism 11, with a reciprocal motion of the primary piston shaft 53 occurring. Since secondarily piston 18 is spring loaded against primary piston 17 (in the manner as well be explained below) movement of primary piston 17 due to rotation of triggering and travel adjustment knob 22 will cause the identical motion of secondary piston 18. Since this is the case, hub channel 23 of primary piston 17 is spaced the identical distance from hub channel 32 of secondary piston 18 regardless of the travel setting of the primary piston 17. Further, since the location of secondary piston 18 is always an identical distance from primary piston 17 (i.e. secondary piston 18 is always oriented in a predetermined position relative to primary piston 17 regardless of the travel setting of primary piston 17). Secondary piston 18 can have inscribed thereon the adjustment calibration rings 52 and have these rings 52 reflect the travel distance setting of primary piston 17.

The fact that hub channel 53 is also located a predetermined distance from hub channel 32 when the actuating mechanism 11 is in the cocked position (this is also true when the actuating mechanism 11 is in its "uncocked" position after completion of both stages of the actuation thereof). The needle 12 of the invention can be standardized. In other words, a standard length inner rod 30 and standard length cannula 36 can be used in the actuating mechanism 11 of the present invention regardless of the travel setting of the primary piston 17, and distal end 40 of cannula 36 will be correctly oriented along inner rod 30 so as to be directly adjacent distal tip 29 thereof when the actuator mechanism 11 is in the cocked position (or the "uncocked" position) regardless of the travel setting of the primary piston 17.

Housing 15 has formed therein an annular groove 62 into which an annular fixation shoulder 63 of the secondary ball housing 64 is inserted. Secondary ball housing 64 is thus fixed into position relative to housing 15 and never moves relative thereto at any time throughout the operation of the actuation mechanism 11.

Secondary ball housing 64 also includes an interior shoulder 65 which is fixedly attached to the distal end of 66 of the primary ball housing 67. Primary ball housing 67 thus becoming fixed relative to housing 15 and never being allowed to move relative thereto at any time during operation of the actuator mechanism 11.

Secondary ball housing 64 includes a generally annular shaped front distal surface 68 upon which the proximal end of primary piston rings 69 and the proximal end of secondary piston spring 70 rests. Further, secondary ball housing 64 includes an generally annular shaped back distal surface 71 upon which rests the distal end of the reset spring 72. Therefore, at least one end of each of the springs 69, 70 and 72 rests against a surface which is fixed relative to housing 15 and never moves at any time during operation of the actuator mechanism 11.

Secondary ball housing 64 further includes a plurality of openings 73 located in uniformally spaced apart relationship around the cylindrical body thereof into each of which is placed a secondary catch ball 74. The catch balls 74 being of a diameter slightly smaller than the diameter of the opening 73 so as to allow them to freely pass therethrough as they are acted upon by other elements included in the inner workings of the actuator mechanism 11. Similarly, a series of uniform spaced apart opening 75 are located circumferentially around the cylindrical body of the primary ball housing 67. A primary catch ball 55 is located in each of the openings 75 and is of a diameter smaller than the diameter of opening 75 to allow them to freely pass through as acted upon by other elements included in the internal workings of the actuator mechanism 11.

The distal end of primary piston spring 69 rests against shoulder 76 of primary piston 17.

The secondary tubular shaft 78 is fixedly attached at its proximal end 79 to the distal end 80 of the second piston extension member 81. The proximal end 82 of second piston extension member 81 surrounds the secondary ball housing 64 and extends slightly proximately of the openings 73 therein. The interior cylindrical surface of the proximal end 82 of the secondary piston extension member 81 includes a plurality of ball notches 83 which extend in a uniformally spaced apart radially orientation. Each ball notch 83 corresponding to an opening 73 and being sized to allow for at least partial entrance of a secondary catch ball 74 therein. Each ball notch 83 is, also slightly larger in size than necessary for acceptance of a secondary catch ball 74 in order to compensate for the proximal and/or distal movements of the secondary piston 18 due to the proximal and/or distal movements of primary piston 17 during the travel adjustment setting process.

The distal end 80 of the secondary piston extension member 81 includes an annularly shaped shoulder 84 upon which rests the distal end of the primary piston spring 69. The secondary piston extension member 81 also includes an annularly shaped distal surface 85, upon which is located an O-ring damper 86.

The primary piston 17 has attached thereto, at its junction between its hub channel 23 and the shoulder 76 of its shaft 53, a tubular, cylindrically shaped spring spacer and guide 87 which functions to prevent entanglement between the primary piston spring 69 and the secondary piston ring 70 and as a guide for the primary piston 17. Slot 77 is located in the cylindrical tubular shaft 78 of the secondary piston 18 in which the hub channel 23 of primary piston 17 slides. Primary piston 17 is prevented from rotating relative to secondary piston 18 due to an extension (not shown) which extends from guide 87 into slot 77 and permanently fixes the relative rotational orientation of primary piston 17 relative to secondary piston 18.

The distal end of the spring spacer and guide 87 includes an annular shoulder 88 upon which rests O-ring damper 86. The O-ring damper 86 functions to dampen the shock of the coming together of primary piston 17 and the secondary piston extension member 81 during the phases of actuation of the actuator mechanism 11.

The proximal end of reset spring 72 abuts the annular distal surface 89 of the generally cylindrically shaped primary release member 90. Blocking surface 91 covers openings 75 in the primary ball housing 67 and forces the primary catch balls 55 to extend into the reduced diameter 54 of the primary piston shaft 53, thus locking the primary piston 17 in its cocked, spring-loaded position.

Similarly, secondary release member 92, which is located so as to be slidably positioned between the primary release member 90 and the secondary ball housing 64, includes a blocking surface 93 which forces the secondary catch balls 74 into the ball notches 83 of the secondary piston extension member 81, thus locking the secondary piston 18 in its cocked, spring-loaded position.

Located just proximally of the blocking surface 93 of the secondary release member 92, is an annular ball notch 94 which is out of alignment with openings 73 in the secondary ball housing 64 when the actuator mechanism 11 is in its cocked position. Located just distally of the notch 94 is a smaller notch 105 which will hold the release member 92 in its locked position until actively forced to move due to the contact of wings 57 with surface 100 of spacer 95.

The proximal end of the secondary release member 92 may include an annular spacer element 95 which extends approximately therefrom in the direction towards the primary travel adjustment washer 56, or may alternatively extend the length shown by spacer 95 without the spacer 95 being used.

Also located at the proximal end of secondary release member 92, and fixed to the interior surface thereof, is a wire retainer 96 which prevents movement of shoulder 97 of the primary release member 90 therepast in the proximal direction, and which also aids in the relocating of the secondary release member 92 to its proper cocked position in a manner as will be explained momentarily.

A cylindrical bushing 98 having angularly shaped pad 99, used for dampening primary piston, attached to its proximal end, may be located around the primary piston shaft 53 and abutted against the proximal end of the primary ball housing 67. Alternatively housing 67 and bushing 98 may be formed as a single unitary member.

As is evident, the actuator mechanism 11 of the present invention is formed as a double locking system. The primary catch balls 55 locking the primary piston 17, and the secondary catch balls 74 locking the secondary piston 18.

As will become evident in the following description of the first and second stages of actuation of the biopsy device 10 the primary piston 17 must necessarily be released from its cocked, spring-loaded, locked position and pass through its pre-set travel or stroke before it is possible for the secondary piston 18 to be released from its cocked, spring-loaded, locked position and travel to a position where it is once again located in the same relative orientation with respect to primary piston 17 as it had prior to actuation of the device 10.

Figure 4B:
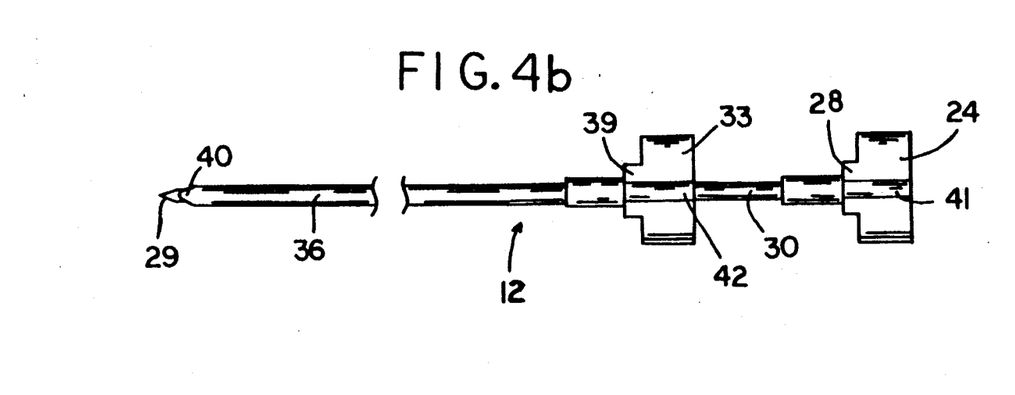
FIG. 4(b) is a top view of the needle portion of the biopsy device as would be oriented when placed in the biopsy device in its cocked position as shown in FIG. 4(a)

As shown in FIG. 4(b), the needle 12 when inserted into the cocked actuator mechanism 11 as shown in FIG. 4(a), the distal end 40 of the cannula 36 is located directly adjacent the distal tip 29 of the inner rod 30, and the hubs 24 and 33 thereof are spaced apart a distance corresponding to the standard relative orientation of hub channel 23 with respect to hub channel 32. As noted above this standard relative orientation (and therefore the distance between hubs 24 and 33 when the actuator mechanism 11 is in the cocked position) is a standard fixed distance which is constant regardless of the travel setting of primary piston 17.

Figure 5A:
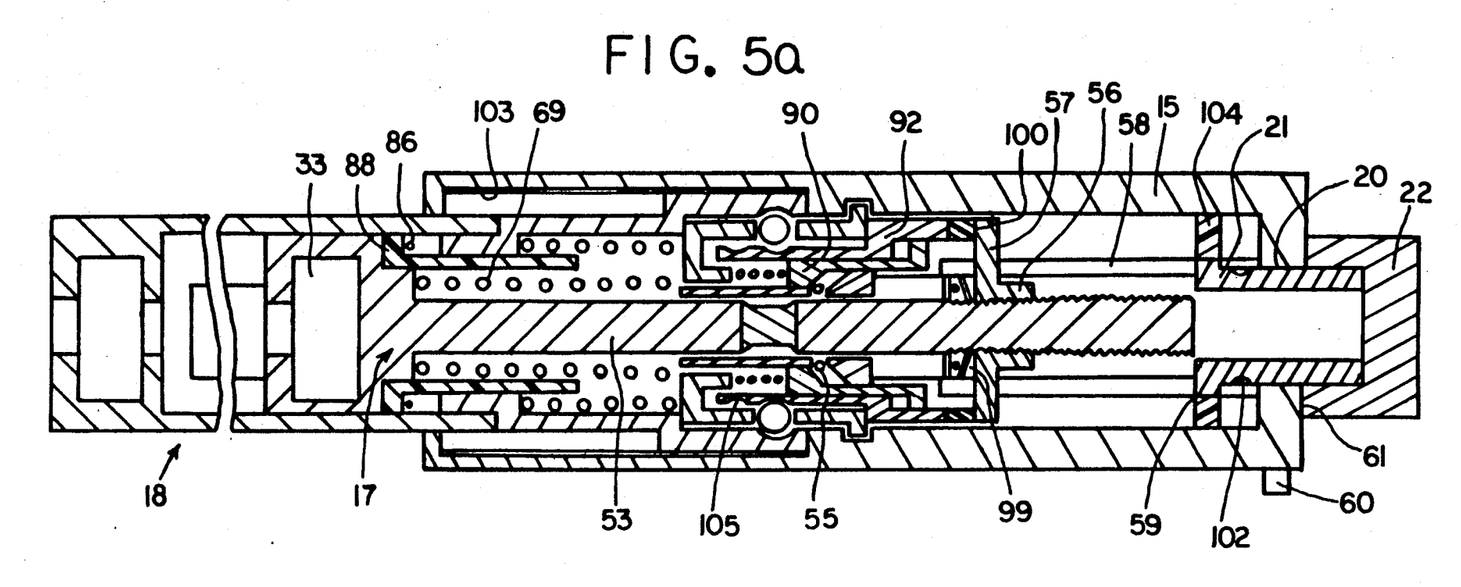
FIG. 5(a) is a cross-sectional view of a biopsy device of the present invention showing the relative positions of the internal components at the completion of the first stage of actuation.

FIG. 5(a) shows the relative orientation of the internal workings of the actuator mechanism 11 at the completion of the first stage of actuation. As can be seen, trigger and travel adjustment knob 22 has been pushed to force trigger and adjustment shaft 21 in the distal direction, which motion causes the distal end surface 100 thereof to push against shoulder 97 of the primary release member 90. Primary member release 90 is thus moved distally a distance sufficient to move locking surface 91 thereof away from the openings 75 in the primary ball housing 67. Primary catch balls 55 are then forced out of the reduced diameter portion 54 of the primary piston shaft 53 due to the force of the primary piston spring 69 which drives the primary piston 17 in the distal direction.

Since primary catch balls 55 are no longer of holding shaft 53 in against the force of the primary piston spring 69, the primary piston 17 moves in a distal direction along with the spring spacer and guide 87 which is fixedly attached thereto and the primary stroke adjustment washer 56 which is threadedly attached thereto.

When primary stroke adjustment washer 56 travels distally a sufficient distance to contact spacer element 95 of the secondary release member 92, the wings 57 thereof then push the secondary release member 92 in the distal direction a sufficient distance to cause the annular ball notch 94 thereof to be oriented directly over the openings 73 of the secondary ball housing 64. The adjustment washer 56 continues to travel in the distal direction until finally being arrested by pad 99 which preferably is comprised of two nylon washers and an O-ring. When adjustment washer 56 is prevented from further forward motion, it subsequently prevents further forward motion of the primary piston 17 and the first stage of actuation is complete.

Figure 5B:
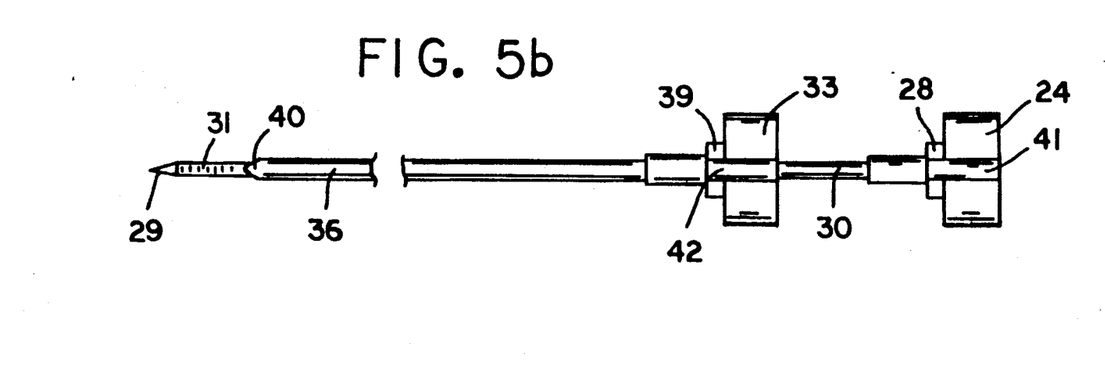
FIG. 5(b) shows the needle of the present invention as it would be oriented if located in the biopsy device when in its configuration shown in FIG. 5(a)

As shown in FIG. 5(b) when the actuator mechanism 11 has completed the first stage of actuation, the inner rod 30 of the needle 12 has extended beyond the cannula 36 such that the predetermined length of sample notch 31 is exposed beyond the sharpened distal end 40 of the cannula 36. Tissue in the target area is therefore allowed to enter the portion of sample notch 31 which is extended beyond the distal end 40 of the cannula 36. Any length of sample notch 31 which fails to extend beyond cannula 36 cannot be accessed by tissue and therefore remains empty. Since the travel of inner rod 30 is directly determined by the travel of primary piston 17, the travel distance pre-set in actuator mechanism 11 for travel of primary piston 17 directly corresponds to the tissue sample size collected in the sample notch 31 of the needle 12.

Figure 6A:
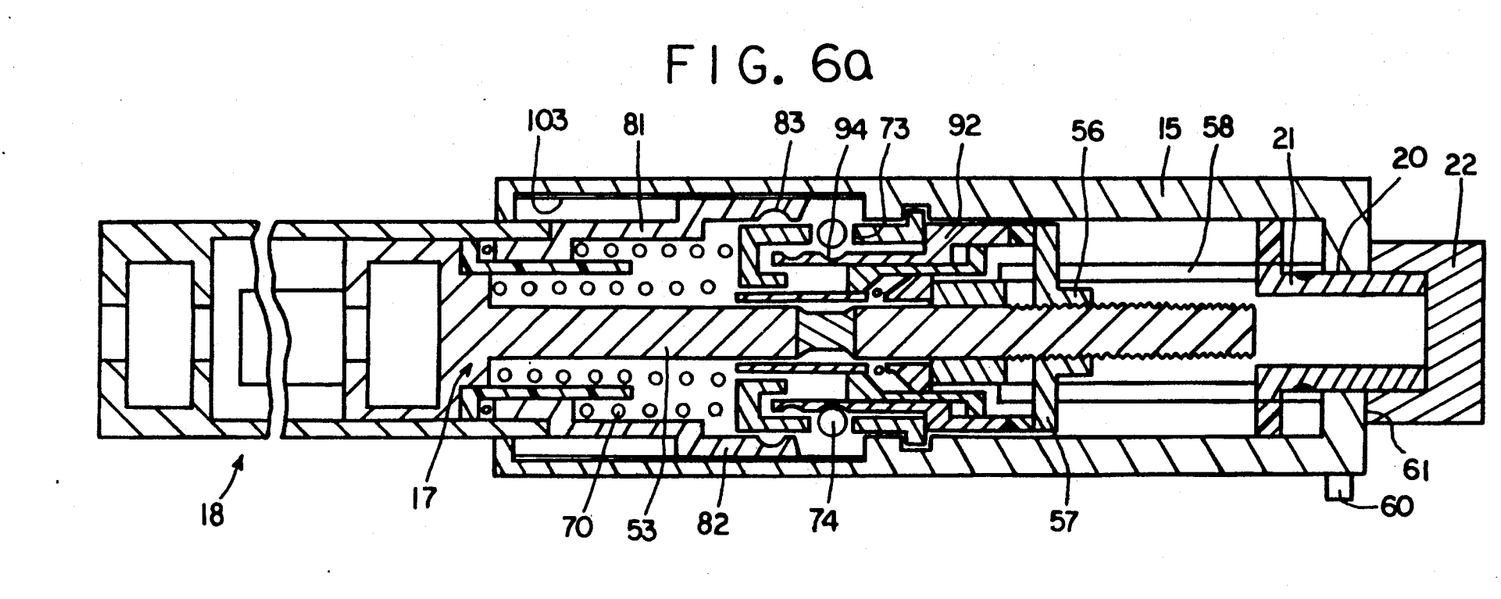
FIG. 6(a) shows a cross-section of the biopsy device of the present invention showing the relative positions of the internal components at the end of the second and final stage of actuation.

Referring now to FIG. 6(a), the second stage of actuation begins immediately upon the completion of the first stage of actuation. Due to the spring-loaded pressure of ball notches 83 against secondary catch ball 74, when the annular ball notch 94 of the secondary release member 92 is located over the opening 73 of secondary ball housing 64, the secondary catch balls 74 are forced radially inwardly into the annular ball notch 94. Since secondary catch ball 74 no longer counteract the spring-loaded force of secondary piston spring 70, the spring 70 forces secondary piston extension member 81 to slide over thin plastic bushing 103 in the distal direction, which in turn forces the tubular shaft 78 of the secondary piston 18 in the distal direction. When the secondary piston 18 arrives at its predetermined orientation relative to primary piston 17, distal surface 85 of the secondary piston extension member 81 is driven into the O-ring damper 86 and prevented from further distal motion by the primary piston 17 (which itself is prevented from further distal motion due to the abutment of adjustment washer 56 against pad 99). When the internal workings of the actuator mechanism 11 arrive at the relative orientation shown in FIG. 6(a) the second and final stage of actuation is complete.

Figure 6B:
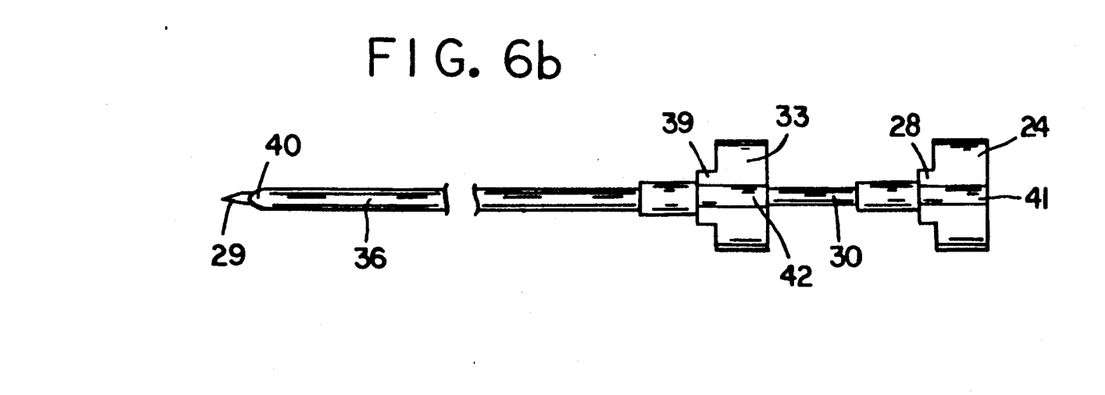
FIG. 6(b) shows the needle oriented in its configuration caused by the secondary stage of actuation as shown in FIG. 6(a).

As shown in FIG. 6(b), the second stage of motion of the actuator mechanism 11 has caused cannula 36 to pass over, and recover sample notch 31. During this motion of cannula 36, the sharpened distal end 40 thereof has severed the tissue sample located in sample notch 31 from surrounding tissue. The cannula 36 then stops its distal motion at a position where the distal end 40 thereof is located directly adjacent the pointed distal tip 29 of the inner rod 30. In this position, the tissue sample is located in sample notch 31 and completely covered and sealed therein due to the positioning of cannula 36 thereover.

Once the tissue sample collection process is completed, the needle 12 can be removed from the actuator mechanism 11 (subsequent to removal of cover 13) and the entire needle 12 can be packaged or otherwise transported if desired to any desired location for subsequent evaluation of the tissue sample. The tissue sample remaining completely in tack inside the needle 12 until removed for examination purposes. It is evident therefore that the needle 12 and the cover 13 can be designed as disposal single use items, and the actuator mechanism 11 can be designed for substantial repetitive use.

It is therefore contemplated that the actuator mechanism 11 be made of durable and precision formable materials such as metal or high strength plastic materials. The needle 12 may be formed of metal also or of any other suitable material which would allow for disposability at minimal expense.

After the actuator mechanism 11 has been completed an actuation cycle, it must be recocked. As explained above, the cocking mechanism is inserted through the hub channels 23 and 32 until end 51 thereof abuts bottom plate 25. The primary piston 17 is then pushed in the proximal direction by the cocking mechanism 14 until ball notches 83 of the secondary piston extension member 81 are again located above the opening 73 of the secondary ball housing 64, and the reduced diameter portion 54 of the primary shaft 53 is again located below the openings 75 in the primary ball housing 67. Reset spring 72 then pushes release member 90 in the proximal direction until locking surface 91 thereof covers the top of openings 75 to force primary catch balls 55 into the reduced diameter portion 54 thus locking the primary piston in its cocked position. The force of the cocking mechanism 14 against the primary piston 17 causing the primary piston spring 69 to become extended and thus spring-loading the primary piston 17 for its next actuation cycle.

Proximal motion of the primary release member 90 due to the reset spring 72 causes shoulder 97 thereof to abut the wire retainer (ring) 96 located in the distal end of secondary release member 92, thus proximal motion of shoulder 97 causes secondary release member 92 to also moved in a proximal direction until locking surface 93 thereof is located under the opening 73 of the secondary ball housing 64. This motion forces secondary catch ball 74 radially outwardly and into ball notches 83 thus locking the secondary piston 18 in its cocked position. The cocking motion of secondary piston 18 causes the secondary piston spring 70 to be tensioned thus spring loading the secondary piston 18 in preparation for another actuation cycle.

Proximal motion of the primary release member 90 due to the reset spring 72 also causes shoulder 97 thereof to abut against distal surface 100 of the triggering and adjustment shaft 21. Triggering an adjustment shaft 21 is therefore moved distally until shoulders 59 thereof abut against the interior surface of the housing 15.

Once the cocking procedure is completed, the interior workings of the actuator mechanism 11 are again oriented as shown in FIG. 4(a) and are prepared for another actuation cycle.

It is to be understood that the above described embodiment is only illustrative of the application of the principles of the present invention. Numerous modifications or alternative arrangements or embodiments may be devised by those skilled in the art without departing from the spirit and scope of the present invention.

I claim:

1. A tissue sampling apparatus comprising:
   an outer elongate cannula having a sharpened distal end for insertion into a sample target area of said tissue;
   an elongate, inner rod having a sample receiving notch adjacent to its distal end, said inner rod being received within said cannula;
   means for extending the distal end of the elongate, inner rod from the distal end of the cannula to penetrate into said tissue in said sample target area;
   means for selectively adjusting the length that the distal end of said inner rod extends from the distal end of said cannula and therefor the depth of penetration of the sample receiving notch of said inner rod into said tissue to expose an adjustable, preselected length of the sample notch to said tissue for an adjustable, predetermined volume of tissue to fill the exposed length of said sample notch;
   means for moving the distal end of the cannula along said inner rod toward the extended distal end of said inner rod and over the previously exposed length of the sample notch to severe tissue located in the sample notch from surrounding tissue and contain the severed tissue in said notch as the distal end of said cannula moves over the notch;
   trigger means and an actuator means, said trigger means, when triggered, causing said actuator means to first actuate the means for extending the distal end of the inner rod into the tissue in said sample target area and then subsequently actuate the means for moving the distal end of the cannula for severing tissue in said notch and recovering the severed tissue;
   said trigger means further being rotatable relative to said actuator means whereby rotation of said trigger means controls the means for selectively adjusting the depth of penetration of the inner rod into said tissue,
   whereby, said means for selectively adjusting the length that the inner rod extends from the end of the cannula into said tissue allows an adjustable, predetermined volume of severed tissue to be recovered from said sample target area.

2. A sampling apparatus according to claim 1 wherein said inner rod has a distal end and a proximal end, said distal end of said inner rod being sharpened and said proximal end of said inner rod including a first hub means, said cannula has a proximal end and a distal end, said proximal end of said cannula including a second hub means, said inner rod being of an length sufficient to allow said distal end thereof to extend beyond the distal end of said cannula while said first hub means of said inner rod extends from the proximal end of said cannula.

3. A sampling apparatus according to claim 2 wherein said means for extending the distal end of said inner rod includes a primary piston means and said means for moving the distal end of the cannula along said inner rod includes a secondary piston means, said first hub means being attachable to said primary piston means, and said second hub means being attachable to said secondary piston means.

4. A sampling apparatus according to claim 3 further including cover means for covering said first and second hub means when said first and second hub means are attached to said primary and secondary piston means, respectively.

5. A sampling apparatus according to claim 4 wherein said first and second hub means include a stabilizing member which contacts said cover means thereby securing said first and second hub means in their proper position when attached to said primary and secondary piston means.

6. A sampling apparatus according to claim 5 wherein said actuator means comprises a primary spring member and a secondary spring member, said primary piston means is attached to said primary spring member, and said secondary piston means is attached to said secondary spring member, whereby when said actuator means is triggered by said trigger means, said primary piston means is first forced into linear motion by said primary spring member, and then subsequently, said secondary piston means is forced to move in a linear direction by said secondary spring member.

7. A sampling apparatus according to claim 6 wherein said means for selectively adjusting the depth of penetration of the sample receiving notch of said inner rod into said tissue is effected by adjusting the amount of linear motion of said primary piston means.

8. A sample apparatus according to claim 7 wherein said primary piston means includes means for limiting the distance of linear movement of said secondary piston means, with said linear movement distance of said secondary piston means being equal to said linear movement distance of said primary piston means.

9. A sampling apparatus according to claim 8 wherein said actuator means further includes a locking means, said locking means preventing said primary spring member and said secondary spring member from forcing said primary piston means, and said secondary piston means respectively, into linear motion when locked thereby, said locking means of said actuator means being releasable in stages corresponding to a first stage wherein said primary piston means is released from said locking means and a second stage wherein said secondary piston means is released from said locking means, said first stage and said second stage occurring serially, with the completion of said first stage occurring simultaneously with the beginning of said second stage.

10. A sampling apparatus according to claim 9 further including cocking means for moving said primary piston means and said secondary piston means into proper orientation relative to said actuator means to allow engagement of said locking means therewith.

11. A method of obtaining a tissue sample from a sample target area including the steps of:

positioning an outer elongate cannula having a sharpened distal end such that the distal end of said cannula is adjacent to said sample target area, extending a distal end of an elongate, inner rod contained in said cannula into the tissue in the sample target area, wherein the inner rod has a sample receiving notch adjacent to its distal end, said step of extending the distal end of said inner rod into the tissue in the sample target area including triggering an actuator means which causes the preselected penetration of said inner rod into the tissue in said target area, adjusting the length that the distal end of the inner rod extends from said cannula to selectively expose preselected, adjustable length of the sample notch from the distal end of said cannula for a predetermined, adjustable volume of tissue to fill the exposed length of said sample notch, wherein the selective adjustment of the depth of penetration of the distal end of said inner rod into the tissue in said sample target area is done by rotating an adjustment means prior to triggering said actuator means, moving the distal end of the cannula along said inner rod toward the extended distal end of said inner rod and over the previously exposed length of the sample notch to sever tissue located in said sample notch from surrounding tissue as the distal end of said cannula moves over said notch to separate said preselected volume of sample tissue from said sample target area, and removing said cannula and inner rod from said sample target area.

* * * * *